United States Patent [19]

Hoiberg et al.

[11] Patent Number: 4,920,055

[45] Date of Patent: Apr. 24, 1990

[54] CONVERSION OF ALCOHOLS TO ALDEHYDES AND HYDROGEN PEROXIDE BY SUBSTRATE AND PRODUCT TOLERANT METHANOL OXIDASES

[75] Inventors: Dane A. Hoiberg, San Clemente; G. Wesley Hatfield, Corona del Mar; Harris S. Moyed; Janice A. Sharp, both of Irvine, all of Calif.

[73] Assignee: American Biogenetics Corporation, Davis, Calif.

[21] Appl. No.: 825,856

[22] Filed: Feb. 4, 1986

[51] Int. Cl.$^5$ .......................... C12P 7/24; C12P 3/00; C12N 9/04; C12N 1/32

[52] U.S. Cl. .................................. 435/147; 435/168; 435/190; 435/247; 435/818; 435/930

[58] Field of Search ............... 435/147, 168, 190, 313, 435/813, 247, 818, 930

[56] References Cited

U.S. PATENT DOCUMENTS 3,997,396 12/1976 Delente .................. 435/240.242
4,416,993 11/1983 McKeown .................. 435/813
4,540,668 9/1985 Hopkins .................. 435/813

OTHER PUBLICATIONS

Greenwood et al., Journal of General Microbiology, 132, pp. 1247–1256, (1986).
Kerley, M.S. et al., (1985), *Science*, 230, 820–822.
Baratti et al., (1978), *Biotech. and Bioengrg.* 20, 333–348.
Levine et al., (1973), *Appl. Microbiol.*, 26, 982.
Ledeboer et al., (1985), *Nuc. Acids Res.* 9, 3063–3082.
Strathman (No. 5, 1985), *Trends in Biotech.*, 3, 112.
Couderc, R. and Baratti, J., (1980), *Biotech. and Bioengrg.* 12, 1155–1173.
Kato et al., (1974), *Agr. Biol. Chem. 38(3)*, 675–677.
Sahm, H. and Wagner, F., (1973), *Eur. J. Biochem.*, 36, 250–256.
Bjurstrom, Ed, (2/18/85), *Chem. Engrg.*, 127–158.
Tani, et al., "The Microbial Metabolism of Methanol", *Agr. Biol. Chem.*, vol. 36, No. 1, pp. 76–83, (1972).
Tani, Y., et al., Production of Formaldehyde by a Mutant of Methanol Yeast, Candida Boidinii S2, J. Ferment. Technol., vol. 63, No. 5, 443–449, 1985.

*Primary Examiner*—John Edward Tarcza
*Attorney, Agent, or Firm*—Knobbe, Martens, Olson & Bear

[57] ABSTRACT

Disclosed is a process for converting alcohols to aldehydes and hydrogen peroxide through the use of a methanol oxidase enzyme. The process involves introducing a lower alkyl or lower alkylene alcohol, such as methanol, ethanol, or allyl alcohol, as an aqueous solution into a reaction zone. Methanol oxidase enzyme that is stable in methanol concentrations of at least 0.5% and formaldehyde concentrations of at least 1.0% is also introduced into the reaction zone, which is maintained at an elevated pressure in contact with an oxygen-containing gas. The preferred methanol oxidase enzyme has the properties of the methanol oxidase enzyme produced by *Hansenula polymorpha* ATCC 34438. Both batchwise and continuous processes are disclosed. Also disclosed is a process in which a catalase is present in the reaction zone to decompose hydrogen peroxide as it is formed, so that the net reaction is the conversion of alcohol to aldehyde. In one aspect of that process, the aldehyde may be removed as a gas and subsequently condensed to an essentially pure liquid.

47 Claims, 3 Drawing Sheets

CONVERSION OF ALCOHOLS TO ALDEHYDES AND HYDROGEN PEROXIDE BY SUBSTRATE AND PRODUCT TOLERANT METHANOL OXIDASES

BACKGROUND OF THE INVENTION

This invention relates to the use of a methanol oxidase (EC 1.1.3.13) enzyme to convert a lower alkyl alcohol such as methanol or ethanol to a lower alkyl aldehyde, such as formaldehyde or acetaldehyde, and hydrogen peroxide, in the presence of oxygen.

The most common industrial process for the production of formaldehyde is the catalytic oxidation of methanol in air at 300°–600° C. in the presence of a silver or a metal oxide catalyst. The resulting product is purified by distillation. Modern processes typically have a stoichiometric yield of about 90%. The value of the formaldehyde produced is roughly three times the value of the methanol consumed. Typical processes for the production of formaldehyde are disclosed in U.S. Pat. Nos. 2,812,309 and 2,849,492. U.S. production of formaldehyde in 1984 was approximately 5.7 billion pounds. Formaldehyde is primarily used in the preparation of polymers, including urea-formaldehyde, phenolic, and melamine polymers.

Perhaps the most common method of synthesizing acetaldehyde is the liquid phase oxidation of ethylene with a palladium chloride catalyst. Acetaldehyde can also be produced by the partial oxidation of ethanol. The value of acetaldehyde per pound is roughly 50% more than the value of ethanol. U.S. production of acetaldehyde in 1983 was roughly 560 million pounds, and worldwide production was over 2.3 billion pounds. Acetaldehyde is an important precursor in the synthesis of a number of products, including acetic acid, acetic anhydride n-butanol, and synthetic flavors.

Hydrogen peroxide ($H_2O_2$) is commonly produced by the oxidation of an alkyl anthrahydroquinone, such as 2-ethyl anthrahydroquinone. In this process, the starting material is oxidized to the quinone, which is subsequently reduced to the starting material by hydrogen in the presence of a palladium catalyst.

In 1984, U.S. production of hydrogen peroxide was about 375 million pounds. The value of hydrogen peroxide on a molar basis is approximately seven times that of methanol. Hydrogen peroxide is widely used as a bleaching and deodorizing agent for textiles and wood pulp, and as an oxidizing agent in chemical processes. It might also be used to render lignocellulosic residues (wheat straw, corncobs and cornstalks) suitable for consumption by ruminant livestock. See M. S. Kerley, et al., *Science* 230, 820–822 (1985).

Several microorganisms have been identified in recent years that have the ability to utilize methanol as a carbon source. One such organism is *Hansenula polymorpha*. The first step in the methanol utilization mechanism of this organism is the aerobic oxidation of methanol into formaldehyde and hydrogen peroxide.

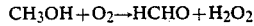

$$CH_3OH + O_2 \rightarrow HCHO + H_2O_2$$

In the in vivo system, the resulting hydrogen peroxide is rapidly decomposed by a catalase into oxygen and water.

The possibility of using methanol oxidase (EC 1.1.3.13) from *Hansenula polymorpha* in a commercial process for the production of formaldehyde from methanol was investigated by Baratti et al. This work is recorded in *Biotechnology and Bioengineering* 10, 333–348 (1978). Using *Hansenula polymorpha* DL-1 (Levine et al., *Appl. Microbiol.* 26, 982 (1973)) the authors studied the activity of the methanol oxidase enzyme in bound and unbound form in catalyzing the conversion of methanol to formaldehyde and hydrogen peroxide. Although the process was successful at very low methanol concentrations, the enzyme was substantially deactivated by methanol concentrations in excess of 100 millimoles per liter. A 100 mM concentration corresponds to an aqueous solution of 0.4 percent methanol by volume. This is below the feedstock concentration of methanol necessary for a commercially viable process.

Another potentially limiting factor related to feedstock concentration is product concentration. In a commercial process, it is important to achieve product concentrations high enough to permit economical separation and recovery of the products. Inactivation of the enzyme by hydrogen peroxide apparently limited the utility of the process disclosed by Baratti, et al.

Accordingly, an objective of the present invention is to provide a process for the enzymatic conversion of alcohol to aldehyde and hydrogen peroxide that permits the utilization of methanol concentrations well in excess of 0.5 percent by volume.

Another objective of the present invention is to provide a process for the enzymatic conversion of alcohol to aldehyde and hydrogen peroxide that permits the buildup of product concentrations in excess of 0.5 percent by volume. The pH may be adjusted with a volatile buffer such as a carbonate or bicarbonate buffer. Ammonium bicarbonate is one preferred buffer.

BRIEF DESCRIPTION OF THE INVENTION

We have discovered that the methanol oxidase derived from a particular strain of *Hansenula polymorpha*, American Type Culture Collection (ATCC) accession number 34438, can be used in commercially feasible processes for the conversion of alcohol to both aldehyde and hydrogen peroxide, utilizing alcohol feedstock and product concentrations of up to 5 percent or higher. This represents more than an order of magnitude improvement over the processes discussed in the prior art.

Thus, in accordance with one aspect of the present invention, there is disclosed a process for the enzymatic conversion of alcohol to both aldehyde and hydrogen peroxide, comprising the step of contacting an aqueous solution of lower alkyl or lower alkenyl alcohol, (i.e., having 5 or fewer carbon atoms) preferably methanol, ethanol, or allyl alcohol, with a methanol oxidase to convert the alcohol to aldehyde and hydrogen peroxide, wherein the amino acid sequence of the methanol oxidase used is substantially the same as that of the methanol oxidase produced by *Hansenula polymorpha* ATCC 34438. Also included within the scope of the present invention is the use of a methanol oxidase in a process for converting a lower alkyl or lower alkenyl alcohol to aldehyde and hydrogen peroxide, wherein the gene encoding methanol oxidase has a base sequence differing from that of the gene of *Hansenula polymorpha* ATCC 34438 only by modifications that do not substantially diminish the alcohol oxidizing properties of that enzyme.

In accordance with preferred embodiments of the present invention, the aqueous feedstock solution of alcohol is at least 0.5 percent or 1 percent alcohol by volume, preferably at least 2 percent or 3 percent alcohol by volume, and most preferably at least 4 or 5 percent alcohol by volume.

In another preferred embodiment of the invention, the product concentration of aldehyde and/or hydrogen peroxide is at least 0.5 percent or 1 percent in aldehyde or hydrogen peroxide by volume, preferably at least 2 percent or at least 3 percent aldehyde or hydrogen peroxide by volume, and most preferably, at least 4 percent or 5 percent aldehyde or hydrogen peroxide by volume. Obviously, in a process involving the continuous introduction of alcohol into the reaction zone to maintain a given concentration of alcohol, product concentrations higher than that given concentration may be achieved over time.

In accordance with another preferred embodiment of the invention, the process for the conversion of alcohol to both aldehyde and hydrogen peroxide includes the step of adding oxygen or an oxygen-containing gas to the reaction mixture. The oxygen is preferably added to the reaction mixture under a pressure of at least 1.5 or 2 atmospheres, and may be recirculated. Low-boiling aldehyde product may be condensed from the recirculating gas.

One process for converting alcohol to aldehyde and hydrogen peroxide within the scope of the present invention comprises mixing an aqueous solution of alcohol with methanol oxidase in a batch-type process. Another process within the scope of the present invention utilizes a continuous process for converting alcohol to aldehyde and hydrogen peroxide with methanol oxidase. In the continuous process, the enzyme may be immobilized to an appropriate support, over which, or through which, the alcohol solution is passed. Alternatively, a semipermeable membrane or filter system may be used to maintain the methanol oxidase in a reaction zone while permitting alcohol to enter the reaction zone and reaction products to leave the reaction zone.

In accordance with still another aspect of the present invention, the process includes the step of separating the aldehyde produced from the hydrogen peroxide produced. One suitable separation technique is distillation, in which the aldehyde is distilled off from the higher-boiling hydrogen peroxide. If catalase is used to decompose the hydrogen peroxide formed in the reaction to oxygen and water, the net product is aldehyde.

In accordance with yet another aspect of the present invention, the above process may be used to convert particular lower alkyl and lower alkenyl alcohols to their respective aldehydes and hydrogen peroxide. Examples are the conversion of ethanol to acetaldehyde and hydrogen peroxide, the conversion of methanol to formaldehyde and hydrogen peroxide, and the conversion of allyl alcohol to acrolein and hydrogen peroxide.

In a particularly preferred embodiment of the present invention, the methanol oxidase enzyme has an amino acid sequence substantially identical to that of *Hansenula polymorpha* ATCC 34438.

In all of the above processes, the pH of the reaction mixture is preferably maintained between about 6.5 and 9, and most preferably between about 7 and 8. The pH may be adjusted with a volatile buffer such as a carbonate or bicarbonate buffer. Ammonium bicarbonate is one preferred buffer.

DETAILED DESCRIPTION OF PREFERRED EMBODIMENTS

Figure 1:
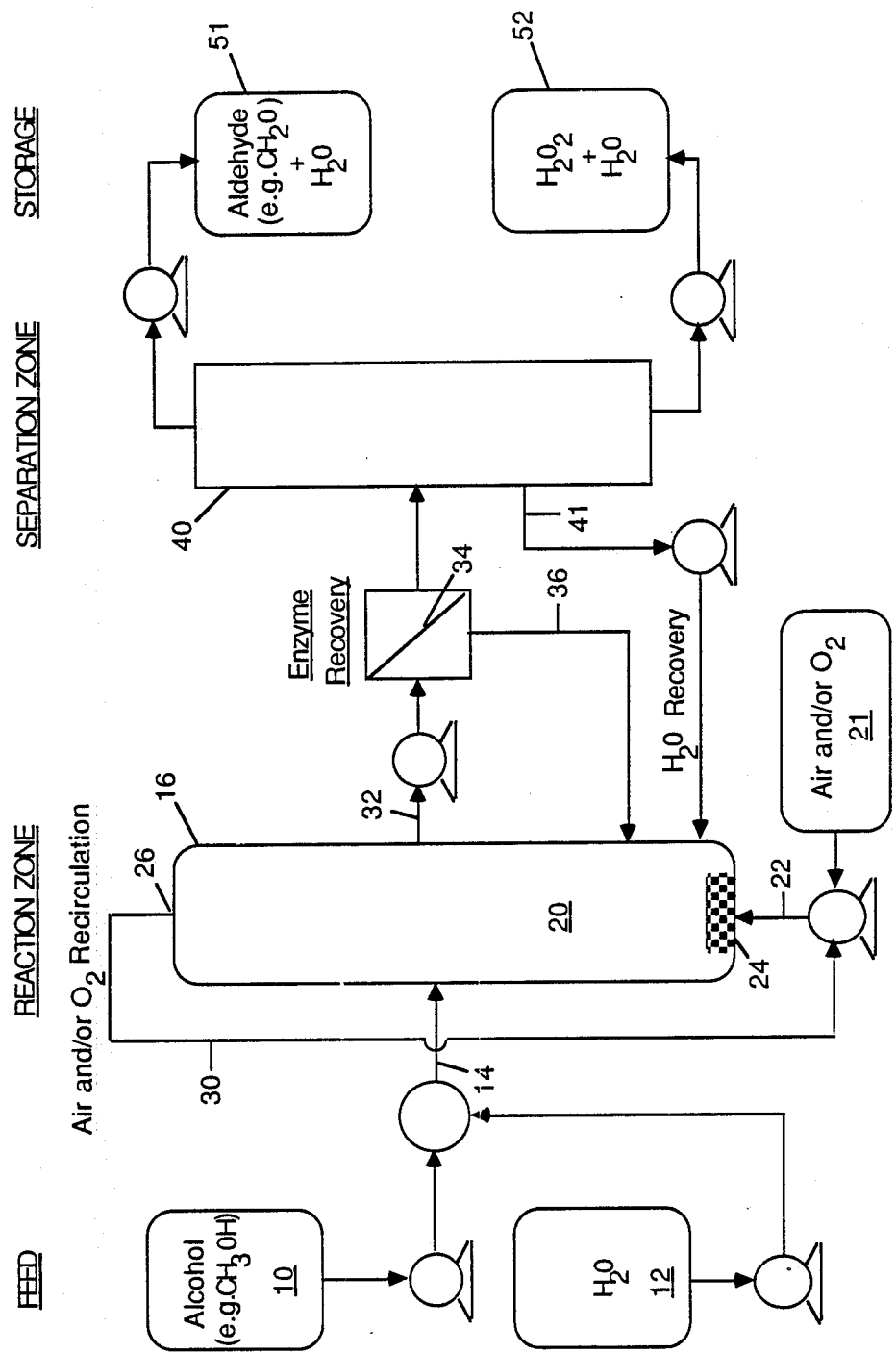
FIG. 1 is a schematic representation of an apparatus for the continuous or batchwise conversion of alcohol to aldehyde and hydrogen peroxide.

The yeast *Hansenula polymorpha* possesses a methanol utilizing pathway which involves the fixation of formaldehyde (derived from methanol) to xyulose-5-phosphate, the conversion of that product into dihydroxyacetone and glyceraldehyde-3-phosphate, and the eventual regeneration of xyulose-5-phosphate. The first step of that pathway involves the oxidation of methanol to formaldehyde and hydrogen peroxide and is catalyzed by methanol oxidase. This methanol oxidase is an octamer of identical subunits with a molecular weight of 70,050, giving a total molecular weight for the enzyme of 560,400. The expression of genes coding for methanol oxidase and the other enzymes involved in the metabolism of methanol is subject to glucose repression. In the presence of methanol, methanol oxidase is induced to a high level in the cell, comprising as much as 20% of the total cell protein. This particular methanol oxidase is attractive for commercial utilization because it contains an autooxidizable cofactor as part of the enzyme complex (FAD) and because, unlike many other bacterial and yeast methanol oxidases, it does not require a readily dissociable cofactor such as NAD which must be regenerated by additional enzymatic reactions.

The preferred methanol oxidases are functionally identical to the methanol oxidase derived from the strain of *Hansenula polymorpha* available from the ATCC under accession No. 34438. The base sequence of the methanol oxidase gene for this organism and the amino acid sequence for the subunits making up this enzyme have been identified for this strain. See Ledeboer et al. (1985) *Nuc. Acids Res.* 9, 3063–3082, which is hereby incorporated by reference. It is, of course, possible to make minor modifications in the base sequence of the gene while retaining the ability of the enzyme to efficiently catalyze the conversion of alcohol to aldehyde and hydrogen peroxide. Whether the modification occurs as a result of mutation or through genetic engineering, such trivially-modified enzymes are considered to be the equivalent of enzymes having the specified amino acid sequence and, thus, are within the scope of the present invention. The methanol oxidase enzymes within the scope of the present invention also include all such enzymes having an active site identical to that of the methanol oxidase of *Hansenula polymorpha* ATCC 34438.

Finally, it is intended that the process of the present invention also include the use of methanol oxidase enzymes derived from *Hansenula polymorpha* strains different from strain ATCC 34438 that retain activity in product concentrations of at least 0.5 percent hydrogen peroxide or aldehyde by volume, preferably at least 0.7 percent or 1 percent hydrogen peroxide or aldehyde by volume, and most preferably at least 2 percent, 3 percent, 4 percent, or 5 percent hydrogen peroxide or aldehyde by volume. A simple screening procedure may be used to identify *Hansenula polymorpha* enzymes having the desired stability. That procedure involves growing up the organism and isolating the enzyme as described hereinafter, and then measuring the ability of the enzyme to catalyze the conversion of alcohol to aldehyde and hydrogen peroxide in predetermined concentrations of alcohol and predetermined concentrations of product. Thus, to screen for methanol oxidase activity suitable for use in the process of the present invention, the purified enzyme (purified to at least to be free of catalase activity) is assayed for its activity in the presence of high concentrations of methanol, i.e., 1%, 2%, 5%, 7% and 10% by volume. It is also assayed for its activity in the presence of high concentrations of products, hydrogen peroxide and formaldehyde. In this reaction the methanol oxidase should be able to produce 2% products when the reactions are initiated in the presence of 1% products and 1% methanol, and 3% products when the reactions are initiated in the presence of 2% products and 1% methanol. It should preferably also be able to produce 4% products when the reactions are initiated in the presence of 3% products and 1% methanol, and 5% products when the reactions are initiated in the presence of 4% products and 1% methanol.

The preferred methanol oxidases are able to convert methanol (and preferably other alcohols) to aldehydes and hydrogen peroxide; they are active in concentrations of methanol of at least 0.5 percent, and preferably at least 1%, 2%, 3%, or 4%: they are active in concentrations of hydrogen peroxide of at least 0.5 percent, and preferably at least 1%, 2%, 3%, or 4%; they are active in concentrations of formaldehyde of at least 1%, 2%, 3%, or 4% they have a turnover number of at least 100, preferably at least 180, and most preferably at least 220 moles product/min./mole of active site; they have a $K_m$ for methanol of 2 mM or less; they have a $K_m$ for oxygen of 0.4 mM or less; they are stable in reaction for a least 1 day: and they are stable on storage for at least 15 days.

A. PREPARATION OF ENZYME

The preferred methanol oxidase enzyme may be produced from a *Hansenula polymorpha* gene that has been cloned and amplified by genetic engineering techniques. However, the preferred technique is simply the growth of *Hansenula polymorpha* and the induction of methanol oxidase synthesis in that organism.

(1) Growth of *Hansenula polymorpha* and Enzyme Induction

Growth media for yeast are well known in the art. *Hansenula polymorpha* may be grown in either a glucose or a methanol medium. A suitable glucose medium may contain, by weight, 0.4% $NH_4Cl$, 0.1% $KH_2PO_4$, 0.1% $K_2HPO_4$, 0.05%, $MgSO_4.7H_2O$, 0.05% yeast extract, and 1% glucose. A suitable methanol medium would contain the same nitrogen, potassium, phosphate, and sulfate sources, together with from 0.5% to 3% by volume methanol.

The growth rates of the yeast on glucose and on methanol are similar. The cell doubling time in glucose is somewhat less than 12 hours. The cell doubling time in methanol is slightly more than 12 hours. When the yeast is grown in a glucose medium, methanol oxidase production is induced by diluting the yeast 1:10 from the glucose medium into a 3% by volume methanol medium and growing to late log phase, approximately 24 hours at 28° C.

In the presence of methanol, the resulting *Hansenula polymorpha* contains as much as 20% of its total cellular protein in the form of methanol oxidase.

(2) Enzyme Purification

Although even a crude cell extract contains sufficient enzyme to catalyze formaldehyde and hydrogen peroxide production, such an extract also includes a catalase (peroxidase) that converts hydrogen peroxide to water and oxygen. Accordingly, some purification of the methanol oxidase enzyme is necessary to remove the catalase in order to achieve optimum yields of hydrogen peroxide.

In the first step of a suitable enzyme purification procedure, the cells are disrupted and homogenized. A phosphate buffer may be used to adjust the pH prior to homogenization to about 7.5. After cell disruption, cell debris can be removed by centrifugation. The supernatant solution represents a cell-free enzyme extract.

A particularly preferred purification technique utilizes an ion exchange column to purify methanol oxidase from the crude cell-free extract. This purification procedure is a relatively fast, inexpensive, and efficient method for producing large quantities of protein in a short period of time. The protein that elutes from a DEAE-cellulose column, for example, is free of cellular catalase. The methanol oxidase from *Hansenula polymorpha* elutes from the DEAE-cellulose, using a salt-gradient elution, at approximately 0.3 M NaCl. At this stage the enzyme is approximately 80-90% pure. It is also possible to shorten this procedure further by eluting methanol oxidase from the column using a batchwise elution rather than a salt gradient. The enzyme will be of a lower purity, but since the only contaminant that can affect the reaction is catalase (which catalyzes the reaction $2H_2O_2 \rightarrow 2H_2O + O_2$) and since catalase does not bind to the DEAE-cellulose under the conditions used, the extraneous contamination will be of little consequence.

One example of an effective ion-exchange purification technique is set forth in Example 1, below.

Example 1: Enzyme Purification

*Hansenula polymorpha* cells are collected by centrifugation 5,000×g, 10 min.) and resuspended in 50 mM potassium phosphate buffer, pH 7.5 (using a ratio of cells:buffer of approximately 1:2). Cells are disrupted in a "Beadbeater" homogenizer for 3 min. total (6 bursts of 30 sec. with 5 min. cooling intervals on ice). The extract is centrifuged for 20 min. at 16,000×g, 4° C., and the supernatant solution is applied to a DEAE-cellulose column which has been equilibrated with 50 mM potassium phosphate buffer, pH 7.5. The column is washed with 50 mM potassium phosphate buffer, pH 7.5, until all unabsorbed Proteins are washed from the column. Methanol oxidase is eluted from the DEAE-cellulose with a linear salt gradient from 0–0.6 M NaCl in 50 mM potassium phosphate buffer pH 7.5. Fractions containing methanol oxidase are pooled and concentrated by precipitation with $(NH_4)_2SO_4$ (40–80% saturation). Purification data are set forth in Table 1.

TABLE 1
PURIFICATION OF METHANOL OXIDASE FROM HANSENULA POLYMORPHA

| Step | Volume (ml) | Protein (mg) | Activity (umol/min/ml) | Total Activity (umol/min) | Specific Activity (umol/min/mg) | Purification (fold) |
|---|---|---|---|---|---|---|
| Extract | 225 | 2.2 | 1 | 225 | 0.44 | — |
| DEAE cellulose | 150 | 0.96 | 10.8 | 1620 | 11 | 25 |
| (NH4)2SO4 | 5 | 20 | 200 | 1000 | 9.9 | 22.5 |

The purity of the enzyme produced in Example 1 is determined by SDS-polyacrylamide gel electrophoresis. The methanol oxidase remaining after the final $(NH_4)_2SO_4$ precipitation step has a purity greater than 95%.

Catalase may be obtained as a by product of the purification of methanol oxidase. The catalase does not bind to the DEAE-cellulose column, whereas the methanol oxidase does. The flow-through of the column, which contains the methanol oxidase activity, is pooled and concentrated by precipitation with 80% (saturation) $(NH_4)_2SO_4$. This catalase has a specific activity of 10,000 units/min/mg, which is approximately 1,000 times more active than methanol oxidase. Therefore, to obtain equal activities of catalase and methanol oxidase, catalase concentrations should be approximately one one thousandth of that of the methanol oxidase used.

B. PROCESS CONDITIONS FOR OXIDATION OF LOWER ALKYL ALCOHOLS

(1) Time, Temperature, and pH.

The methanol oxidase produced by the preferred Hansenula polymorpha exhibits temperature stability over a wide range of temperatures, from 25° C. to 37° C. Thus, for converting methanol to formaldehyde, little or no energy input in the form of heat is necessary in the reaction step.

The enzyme also retains activity over a pH range of from 6.5 to 9.0. (The enzyme is unstable at acidic pH.) The preferred process pH is from 7.0 to 8.0, and a pH of 7.5 is particularly preferred. In certain processes, it may be desirable to use a relatively volative buffer, such as $NH_5CO_3$, which can be removed from product by distillation in the purification step. The particular buffer used has some effect on enzyme activity, as shown in Table 2.

TABLE 2
ACTIVITY OF METHANOL OXIDASE IN DIFFERENT BUFFERS

| Buffer(pH 7.5) | Concentration (M) | Relative Rate |
|---|---|---|
| K2HPO4/KH2PO4 | 0.1 | 100 |
| NaHCO3 | 0.05 | 61 |
| NaHCO3 | 0.01 | 53 |
| NH5CO3 | 0.05 | 76 |
| NH5CO3 | 0.01 | 57 |
| None | | 57 |

The preferred buffers are phosphate and carbonate or bicarbonate buffers, including potassium phosphate, sodium bicarbonate, and ammonium bicarbonate, all adjusted to pH 7.5.

Although the preferred methanol oxidase enzyme exhibits its highest affinity for methanol, it also has a significant degree of activity on other lower alkyl and lower alkylene alcohols. Straight chain alcohols of four or fewer carbon atoms are particularly preferred. Aside from methanol, the enzyme exhibits greatest activity with ethanol and allyl alcohol, converting them, respectively, to acetaldehyde and acrolein. The specificity of methanol oxidase to various substrates is set forth in Table 3.

TABLE 3
SUBSTRATE SPECIFICITY OF METHANOL OXIDASE

| Substrate | Relative Activity |
|---|---|
| Methanol | 100 |
| Ethanol | 67 |
| n-Propanol | 19 |
| Isopropanol | 0 |
| n-Butanol | 12 |
| Isobutanol | 0 |
| Isoamyl alcohol | 0 |
| Allyl alcohol | 65 |
| Glycerol | 0 |

(2) Enzyme Productivity

The methanol oxidase from Hansenula polymorpha ATCC 34438 has a $K_m$ for methanol of 2.0 mM and a turnover number of 220 moles products/min./mole active site (i.e., 1 g of enzyme produces approximately 0.1 g each of $CH_2O$ and $H_2O_2$ per min.). These values are determined at dilute enzyme concentrations (<5 ug/ml) where reaction rates are linear with respect to time and enzyme concentration. At higher enzyme concentrations under normal laboratory conditions, oxygen becomes rate limiting. This is demonstrated by the fact that when identical reaction vessels, each containing 1 ug/ml of enzyme are compared, where one of the reaction vessels has been shaken to increase aeration, and the other has been left stationary, different rates of product formation are observed. This indicates the desirability of introducing oxygen into the reaction mixture to obtain maximum reaction rates at high enzyme concentrations.

(3) Stability of Methanol Oxidase in the Presence of Methanol

Unlike the methanol oxidase enzymes that have been studied in connection with prior art processes, the methanol oxidase from Hansenula polymorpha ATCC 34438 exhibits remarkable stability in the presence of methanol and reaction products. Reaction rates for methanol oxidase remain linear in the presence of methanol up to a concentration of approximately 10% methanol (by volume). Eighty percent activity is retained at methanol concentrations as high as 30% (by volume). Accordingly, commercially viable processes within the scope of the present invention may use a feedstock concentration of methanol of at least 0.5% by volume, preferably at least 1%, 2%, or 3% by volume, and most preferably at least 4% or 5% by volume. Concentrations of 10% or 20% may also be used with some loss of enzyme activity.

(4) Enzyme Activity as a Function of Enzyme Concentration

The preferred methanol oxidase from *Hansenula polymorpha* is stable over a broad range of enzyme concentrations At enzyme concentrations from 1 to 1000 ug/ml, reaction rates remain linear for several hours, even in concentrations of up to 10% methanol by volume.

When using unbound enzyme in the process of the present invention, the concentration of enzyme in the reaction zone is preferably from 0.1 ug/ml up to 1000 ug/ml. In some applications, the lower limit of enzyme concentration may be 1 ug/ml or 10 ug/ml, and the upper concentration limit may be 100 ug/ml or 500 ug/ml.

(5) Activity of Methanol Oxidase and Product Stability in the Presence of High Concentrations of Reaction Products Experiments were conducted to ascertain the stability of the preferred methanol oxidase in high concentrations of products. All concentrations are on a volume basis. A first reaction was initiated at 1% methanol and 0% product (0% hydrogen peroxide and 0% formaldehyde) and the increase in product formed was determined as a function of time. A second reaction was initiated in the presence of 3% hydrogen peroxide, 3% formaldehyde, and 1% methanol. In the first reaction, the product concentration rose from 0% to 1% in slightly more than four hours and remained stable at 1% until termination of the experiment at 20 hours. In the second reaction, product concentration increased from 3% to 4% in a period of about 5 hours, and remained stable until the termination of the experiment at 20 hours. This 1% increase in the product concentration in each experiment is a stoichiometric increase, indicating substantially complete conversion of methanol into product. This demonstrates that the methanol oxidase enzyme remains active in product concentrations up to 4% and that the reaction goes to completion and that the products are stable under these conditions.

(6) Introduction of Oxygen into the Reaction Zone

In the enzymatic oxidation of alcohol to aldehyde and hydrogen peroxide of the present invention, oxygen molecules ($O_2$) are stoichiometrically consumed in the conversion process. Thus, for every mole of methanol or other alcohol converted into product, one mole of $O_2$ is consumed from the reaction mixture. Even at enzyme concentrations of as low as 5 ug/ml on a laboratory scale, the diffusion of oxygen into the reaction mixture becomes rate-limiting. Accordingly, large-scale production processes utilizing high enzyme concentrations significantly benefit from aeration of the reaction mixture.

Direct aeration, such as sparging or bubbling air or other oxygen-containing gas through the reaction mixture, represents one alternative for supplying the necessary oxygen. This process, however, can result in losses of the relatively volatile aldehyde products. In some applications, such aldehyde loss may be tolerated because of the relatively greater economic value of the hydrogen peroxide. However, in most cases expelling aldehydes such as formaldehyde into the environment is not desirable because they are unhealthful to humans and animals.

One method for avoiding aldehyde loss is oxygen enrichment of the feedstock prior to introduction into the reaction zone.

In accordance with Charles' law, the amount of gas that may be dissolved in a liquid is directly proportional to the partial pressure of that gas. Thus, more oxygen becomes dissolved in a liquid when the gas and the liquid are under pressure, and more oxygen becomes dissolved in the liquid from aeration with pure oxygen than from aeration with air. The rate of absorption of the gas into the liquid is also dependent on the surface area of the gas/liquid interface. One technique for maximizing the surface area is the minimization of the bubble size when the gas is bubbled through the liquid.

Oxygenation may be accomplished by bubbling a gas containing oxygen through the alcohol solution. The higher the concentration of oxygen in the aerating gas, the more oxygen becomes dissolved in the liquid. Large quantities of oxygen may be dissolved by increasing the pressure of the gas above ambient pressure in the oxygenation step.

For example, in one preferred process, the oxygenation step takes place within a pressurized chamber. That chamber may be the same as the reaction chamber or the reaction zone. If oxygenation under pressure takes place outside the reaction zone, it is desirable to also maintain the reaction zone at an elevated pressure to prevent $O_2$ effervescence of the reaction mixture. This will also serve to maintain the aldehyde in solution.

Various suitable techniques for oxygenating liquids are disclosed in U.S. Pat. Nos. 4,067,696, 4,182,739, and 4,138,288.

In one embodiment of a continuous process, oxygen-enriched liquid flows continuously into the reaction zone. The water-alcohol feedstock mixture may be enriched as discussed above. If substantial dilution of the alcohol feedstock is necessary prior to introduction thereof into the reaction zone, the diluting water itself may be separately oxygenated.

Similarly, in a batch-type process, the entire batch of methanol and water may be oxygenated prior to introduction into the pressurized reaction zone or combination with the methanol oxidase enzyme. Alternatively, a continuous stream of oxygenated water and/or methanol solution may be introduced into the reaction zone, even in the batch-type process.

Although oxygenation of the reaction mixture outside the reaction zone is possible, the preferred oxygenation method is direct oxygenation of the reaction mixture in the reaction zone. In addition to simplifying the apparatus, this also permits the availability of greater amounts of oxygen because the oxygen consumed in the reaction is continuously replenished. Aldehyde loss may be avoided by recirculation of the gas leaving the reaction zone, and/or by sending the gas leaving the reaction zone through a condensation chamber to separate the aldehyde from the oxygen.

(7) Oxidation of Lower Alkyl Alcohol in the Reaction Zone

In the reaction zone, the process conditions of pH, enzyme concentration, methanol concentration, and product concentration established above are employed. The average residence time in the reaction zone is, of course, dependent on all these factors to some extent. However, at a pH of 7.5, the optimal average residence time in the reaction zone is primarily a function of the oxygen concentration and the enzyme concentration.

The concentration of the enzyme and substrates determine the time that the reaction will take to be completed. This time is ultimately dependent on the concentration of oxygen that can be delivered to the reaction zone. Under non-limiting conditions one mole of enzyme requires 1760 moles of oxygen per minute to convert 1760 moles of methanol per minute to 1760 moles of formaldehyde and 1760 moles of hydrogen peroxide. To saturate the enzyme with oxygen, an oxygen concentration of approximately 4 mM is required (since the $K_m$ of methanol oxidase for oxygen is approximately 0.4 mM). At concentrations of 4 mM oxygen the maximum reaction rate of the enzyme is achieved. At 4 mM oxygen 2.2 umoles/liter of enzyme will convert 4 mmoles of methanol to 4 mmoles of formaldehyde and 4 mmoles of hydrogen peroxide per minute provided the oxygen concentration can be maintained at 4 mM. However, at standard temperature and pressure, the concentration of oxygen in air-saturated buffer is approximately 0.2 mM, which is approximately one twentieth of the concentration of oxygen required to give maximum reaction rate of the enzyme. Therefore, the oxygen concentration of the buffer may advantageously be increased by pressurizing the reaction zone to maintain a high reaction rate. Thus, it should be readily apparent that the time required in the reaction zone is directly related to the rate at which oxygen can be delivered.

In a continuous process, some means of retaining the methanol oxidase in the reaction zone is preferable. Enzymes may be immobilized by physical adsorption to DEAE-cellulose or ion-exchange material. Under the conditions of Example 1, the DEAE-cellulose column (or other adsorbents) following the washing step may itself constitute the reaction zone, because the enzyme is bound to the DEAE-cellulose or other adsorbent. Thus, crude cell extract may be simultaneously purified and immobilized to an adsorbent under the conditions of Example 1. This adsorbent:enzyme complex may then be used in the reaction zone.

As an alternative to using bound enzyme, a semipermeable membrane or ultrafiltration material may be provided as the downstream boundary of the reaction zone. A large number of semipermeable membranes and ultrafiltration materials are known, and the selection criteria for a suitable product are simple: it must pass small molecules such as lower alkyl or alkenyl aldehyde, hydrogen peroxide, and buffers, and it must retain the relatively large methanol oxidase (which has a molecular weight of about 560,400). Suitable materials include cellulose and regenerated cellulose membranes, and ultrafilters silicone membranes, and any other conventional dialysis or ultrafiltration material. Other criteria that must be considered in the selection of membranes or filtration material suitable for use in the reactor are: it should not be reactive with the substrate, (alcohol), or the products (aldehyde and hydrogen peroxide); it must be able to withstand the pressure to which it is subjected in the reaction zone without breaking; and it must have a flow rate that does not limit or determine the residence time in the reaction zone. Dialysis membranes meet the criteria of non-reactivity and are sufficiently strong to maintain increased pressure; however, the flow rate through standard membranes is relatively slow. The flow rate may be increased by using membranes with greatly increased pore sizes. Cellulose acetate membranes are particularly appropriate. Since the methanol oxidase has a molecular weight of 560,400, a membrane with a pore size that would retain species having a molecular weight greater than 250,000 could be used. Other membranes that could be used include ultrafiltration membranes such as "Amicon" membranes. "Amicon" is a trademark of Amicon Corp. for its YM100 ultrafiltration membranes. (This particular membrane has the disadvantage of binding the enzyme.) Also, an ultrafiltration system for recovering enzyme from the reaction zone may be preferred for some applications.

In addition to the semipermeable membrane or ultrafilter at the outlet of the reaction zone, a second semipermeable membrane or ultrafilter may be provided at the inlet to the reaction zone. This second semipermeable membrane or ultrafilter may be eliminated, however, in an apparatus where a continuous influx of feedstock prevents back-contamination from the reaction zone. A conventional check valve may be used in place of the second semipermeable membrane or filter.

Examples for batch-type and continuous reaction processes are set forth in Examples 2 and 3, respectively:

Example 2: Batch-Type Conversion of Methanol to Formaldehyde and Hydrogen Peroxide Methanol oxidase from *Hansenula polymorpha* ATCC 34438 is obtained from Example 1. Enzyme is added to a 10 liter reaction vessel containing an aqueous solution of 4% methanol by volume in sufficient quantities to give an enzyme concentration of 100 ug/ml. The aqueous solution is buffered to pH 7.5 with a 0.1 molar potassium phosphate buffer. The vessel is maintained at 27° C. at a pressure of 70 psi. Agitation and oxygen replenishment are provided by bubbling oxygen continuously through the reaction mixture at the rate of 4 mmoles $O_2$/min. After 70 hours, the reaction has gone to completion. The contents of the reaction vessel are passed through a tubular cellulose dialysis membrane having a molecular weight cut-off of 50,000 (Spectra Por brand; available from Pierce Chemical Co.). The enzyme-free dialysate contains approximately 4% by volume hydrogen peroxide and 4% by volume formaldehyde

Example 3: Continuous Conversion of Methanol to Formaldehyde and Hydrogen Peroxide In a continuous process for the conversion of methanol to formaldehyde and hydrogen peroxide, 10 l. 4% by volume aqueous methanol solution is added to a reaction vessel. The solution is buffered to pH 7.5 with a potassium phosphate buffer (0.1 molar). 1.0 g methanol oxidase enzyme from Example 1 is added, providing an enzyme concentration of 100 ug/ml in the reaction vessel. The reaction vessel is pressurized with oxygen to 10 atmospheres, and 4 mmoles/min. oxygen is sparged through the mixture. The gas is removed from the top of the reaction vessel. The gas is then recirculated through the reaction vessel. Air or oxygen is added to the recirculated gas in order to maintain excess oxygen in solution. An ultrafiltration material having a molecular weight cut-off of 100,000 is provided at the inlet and at the outlet of the reaction vessel. Buffered aqueous methanol solution containing 4% methanol by volume is continuously introduced into the reaction zone, at the rate of 2.5 ml/min the reaction products are continuously removed from the reaction vessel through the ultrafiltration material. The ultrafiltration material at the outlet of the reaction vessel is periodically backflushed to remove enzyme accumulating thereon. That enzyme is then recirculated into the reaction vessel. Fresh enzyme is added to the reaction vessel at the rate of 0.5 g/day to maintain the active enzyme concentration at approximately 100 ug/ml. The reaction mixture removed from the vessel contains approximately 4% formaldehyde, 4% hydrogen peroxide, and a small percentage of methanol.

C. SEPARATION OF REACTION PRODUCTS

The products may be separated from each other by distillation. The boiling point of formaldehyde in aqueous solution (formal) is 96° C. at atmospheric pressure and that of hydrogen peroxide is 152° C. at atmospheric pressure. Any methanol that may still be unreacted and therefore still remains in the product mixture would distill off with formaldehyde. Further separation of the methanol and formaldehyde is ordinarily not required since methanol is commonly added to formaldehyde solutions as a stabilizer. Therefore, the purification step preferably involves distilling off formaldehyde and methanol and water at approximately 100° C. The remaining hydrogen peroxide can be further concentrated by distilling off the remaining water as required.

In addition to distillation techniques, separation of aldehydes from hydrogen peroxide may be accomplished by using prevaporation membranes or other membrane processes such as those described by Strathman, *Trends in Biotechnology*, 3, 112, (No. 5, 1985). Super-critical fluid extraction systems such as those manufactured by Milton Roy Company, 201 Ivyland Road, Ivyland, PA 18974-0577 also may be used to separate reaction products.

D. PROCESS MODIFICATIONS

The processes of Example 2 and 3 may be modified in a number of ways to produce different products, as shown in Examples 4–12.

Example 4: Conversion of Methanol into Formaldehyde

The processes of Examples 2 and 3 are repeated, but 0.1 ug/ml catalase obtained from Example 1 is added to the reaction mixture. Under these conditions the catalase converts the hydrogen peroxide produced to oxygen and water. For every mole of oxygen consumed in the methanol oxidase reaction, 0.5 moles of oxygen are released in the catalase reaction. By the inclusion of methanol in the reactions the requirement for added oxygen is reduced. The only end product produced is formaldehyde. This ordinarily will require no further purification, although distillation, or other processes described in Example 3, may be used to concentrate the product.

Example 5: Conversion of Ethanol into Acetaldehyde and Hydrogen Peroxide

The processes of Examples 2 and 3 are repeated, substituting ethanol for methanol. The methanol oxidase concentration is increased to 150 ug/ml and the flow rate and reaction time remain the same as in Example 3. The reaction products are acetaldehyde and hydrogen peroxide.

Example 6: Conversion of Ethanol into Acetaldehyde

The processes of Example 5 are repeated, and catalase is included in the reaction vessel as set forth in Example 4. Under these conditions, the catalase converts the hydrogen peroxide produced to oxygen and water. At the end of the reaction the only product is acetaldehyde. This ordinarily will not require further purification, although distillation may be used to concentrate the product.

Example 7: Conversion of Allyl Alcohol into Acrolein and Hydrogen Peroxide

Methanol oxidase can be used to convert allyl alcohol into acrolein and hydrogen peroxide. The processes of Examples 2 and 3 are repeated, substituting allyl alcohol for methanol to produce acrolein and hydrogen peroxide. The methanol oxidase concentration is increased to 200 ug/ml the time of Example 2 is maintained at 70 hours, and the flow rate of Example 3 into the reaction vessel is maintained at approximately 2.5 ml/min. At the end of the enzyme reaction the products of the reaction are separated by distillation. The boiling point of acrolein is 52° C. at atmospheric pressure.

Example 8: Conversion of Allyl Alcohol into Acrolein

It is possible to produce acrolein alone in the reaction of Example 7 by introducing catalase as well as methanol oxidase into the reaction vessel. The process of Example 4 is repeated, substituting allyl alcohol for methanol, increasing the methanol oxidase concentration to 150 ug/ml and maintaining reaction time in the batch-type process at 70 hours, with a flow rate in the continuous-type process of 2.5 ml/min. Under these conditions, the catalase converts the hydrogen peroxide produced to oxygen and water. At the end of the reaction, the only product is acrolein. This does not require further purification, although distillation may be used to concentrate the product. The boiling point of acrolein is 52° C. at atmospheric pressure.

Example 9: Conversion of n-Propanol into Propionaldehyde and Hydrogen Peroxide Methanol oxidase can be used to convert n-propanol into propionaldehyde and hydrogen peroxide. The processes of Examples 2 and 3 are repeated, substituting n-propanol for methanol. The methanol oxidase concentration is increased to 526 ug/ml and the other reaction conditions of Examples 2 and 3 are maintained. At the end of the enzyme reaction the products of the reaction can be separated by distillation. The boiling point of propionaldehyde is 49° C. at atmospheric pressure.

Example 10: Conversion of n-Propanol into Propionaldehyde

It is possible to produce propionaldehyde alone in the reaction of Example 9 by introducing catalase as well as methanol oxidase into the reaction vessel. Thus, the process of Example 4 is repeated, substituting n-propanol for methanol. The methanol oxidase concentration of Example 2 is increased to 526 mg/ml, and the liquid flow rate into the reaction vessel of Example 3 is maintained at 2.5 ml/min. Under these conditions, the catalase converts the hydrogen peroxide produced to oxygen and water. At the end of the reaction the only product is propionaldehyde. This does not require further purification, although distillation may be used to concentrate the product.

Example 11: Conversion of n-Butanol into Butyraldehyde and Hydrogen Peroxide Methanol oxidase can be used to convert n-butanol into butyraldehyde and hydrogen peroxide. Thus, the processes of Examples 2 and 3 are repeated, substituting n-butanol for methanol. The enzyme concentrations in each instance are increased to 850 ug/ml. At the end of the enzyme reaction the products of the reaction can be separated by distillation. The boiling point of butyraldehyde is 74.8° C. at atmospheric pressure. However, since butyraldehyde is soluble in water at 25° C., separation might be possible by reducing the temperature, until phase separation occurs and separating the phases.

Example 12: Conversion of n-Butanol into Butyraldehyde

It is possible to produce butyraldehyde alone in the reaction of Example 11 by introducing catalase as well as methanol oxidase into the reaction vessel. The process of Example 11 is repeated, except that 0.1 ug/ml. catalase is also introduced into the reaction vessel. Under these conditions the catalase converts the hydrogen peroxide produced to oxygen and water. At the end of the reaction the only product is butyraldehyde. This does not require further purification, although distillation may be used to concentrate the product. The boiling point of butyraldehyde is 74.8° C. at atmospheric pressure. However, since butyraldehyde is only soluble in water above 25° C., separation is possible by reducing the temperature until phase separation occurs and separating the phases.

E. PROCESS APPARATUS

A suitable apparatus for the continuous-type conversion of alcohol into aldehyde and hydrogen peroxide in accordance with the present invention is shown schematically in FIG. 1. An alcohol source 10 and a water source 12 are provided. An inlet line 14 introduces alcohol and water into a reaction zone 16. In FIG. 1, the reaction zone 16 also serves as an aeration or oxygenation chamber. The reaction zone 16 is preferably a pressured chamber or container or a plurality of chambers or containers. The reaction zone may alternatively comprise an elongated structure. One example of such a structure is a tube. The reaction zone 16 contains a reaction mixture 20. This reaction mixture contains water, alcohol that is introduced into the reaction zone through inlet line 14, methanol oxidase enzyme, and oxygen. Due to the action of the methanol oxidase enzyme on the alcohol, the reaction mixture 20 also contains aldehyde and hydrogen peroxide.

Means such as gas inlet 22 are provided for introducing an oxygen-containing gas from an oxygen source 21 into the reaction zone 16. This gas is preferably oxygen gas, $O_2$. The reaction zone 16 is ordinarily pressurized to increase the rate and degree of oxygen dissolving into the reaction mixture 20. The preferred oxygenation technique is a sparging technique. The reaction zone 16 may advantageously include porous material 24 or other conventional material for dispersing the oxygen as bubbles throughout the reaction zone 16. Gas is removed from the reaction zone 16 through the gas outlet 26. Means 30 for recirculating gas from the gas outlet 26 back to the gas inlet 22 may also be provided. Such a recirculating means 30 has the advantage of both conserving oxygen and reintroducing any vaporized aldehyde back into the reaction zone 16 and the reaction mixture 20. Recirculation also prevents expelling unhealthful products, such as formaldehyde, into the environment. Inside the reaction zone 16 or connected to the reaction zone 16 is preferably a means for agitating or mixing the reaction mixture 20. In FIG. 1, the agitation means is the porous material 24 and the oxygen-containing gas passing through the porous material 24 to form bubbles that continuously agitate and mix the reaction mixture 20 in the reaction zone 16.

The reaction zone 16 is bounded at its outlet 32 by an enzyme recovery means 34. The enzyme recovery means 34 may be a dialysis membrane or an ultrafiltration material. The enzyme recovery means 34 is capable of passing species of small molecular weight, such as aldehydes and hydrogen peroxide, while retaining high molecular weight species, particularly the methanol oxidase enzyme used in the present invention, which has a molecular weight of 560,400. In order to prevent a flow-restricting accumulation of enzyme on the enzyme recovery means 34, the flow rate per unit area of the enzyme recovery means 34 is kept low. For any given throughput, this is done by making the semipermeable membrane very large. Periodically, the enzyme recovery means may be washed to remove accumulated enzyme. This can be done by introducing a backflow of liquid through the enzyme recovery means 34 or by directing a liquid flow across, rather than through, the enzyme recovery means 34. Enzyme recovered from the enzyme recovery means 34 is recycled back into the reaction zone 16 through a line 36.

From the reaction zone 16, the aldehyde and hydrogen peroxide produced in the reaction zone pass through the outlet 32 and the enzyme recovery means 34 into a separation zone 40. The separation zone 40 may comprise a distillation apparatus for separating aldehyde from hydrogen peroxide. In practice, more volatile aldehydes can be separated from the hydrogen peroxide as a gaseous mixture. In the case of formaldehyde, this gaseous mixture also contains water and small quantities of methanol. In the case of formaldehyde no further purification will ordinarily be necessary, despite the presence of methanol and water in the end product in vessel 51, because formaldehyde is ordinarily sold as an aqueous solution and that aqueous solution is usually stabilized with small quantities of methanol.

In the separation step, the hydrogen peroxide is removed from the separation zone as an aqueous solution to storage vessel 52. Hydrogen peroxide is ordinarily sold as an aqueous solution but it also may be further concentrated using conventional techniques if desired. With suitable separation apparatus some water is recovered and reintroduced through recirculation line 41.

A batch-type process according to the present invention may also be practiced with the apparatus of FIG. 1. Water, alcohol, and enzyme are introduced into the reaction zone 16 through inlet line 14 to form a reaction mixture 20 and to fill up the reaction zone 16 to the desired level. The reaction mixture 20 remains in the reaction zone 16, with an oxygenating gas being introduced into the reaction zone 16 through gas inlet 22 and porous material 24. The gas is removed from gas outlet 26 and recirculated through recirculation means 30. The bubbling of the oxygen-containing gas through the reaction mixture 20 provides agitation and mixing so that the reaction mixture 20 is substantially homogeneous. When the reaction has gone to the desired stage of completion, the reaction mixture 20 comprises water, aldehyde, and hydrogen peroxide, with little or no alcohol present. The reaction mixture 20 is then removed from the reaction zone 16 through the outlet 32. The enzyme is removed from the reaction mixture 20 by the enzyme recovery means 34, and the reaction mixture proceeds into the separation zone 40. The reaction zone 16 may then be refilled with reaction mixture 20, and the process repeated.

Figure 2:
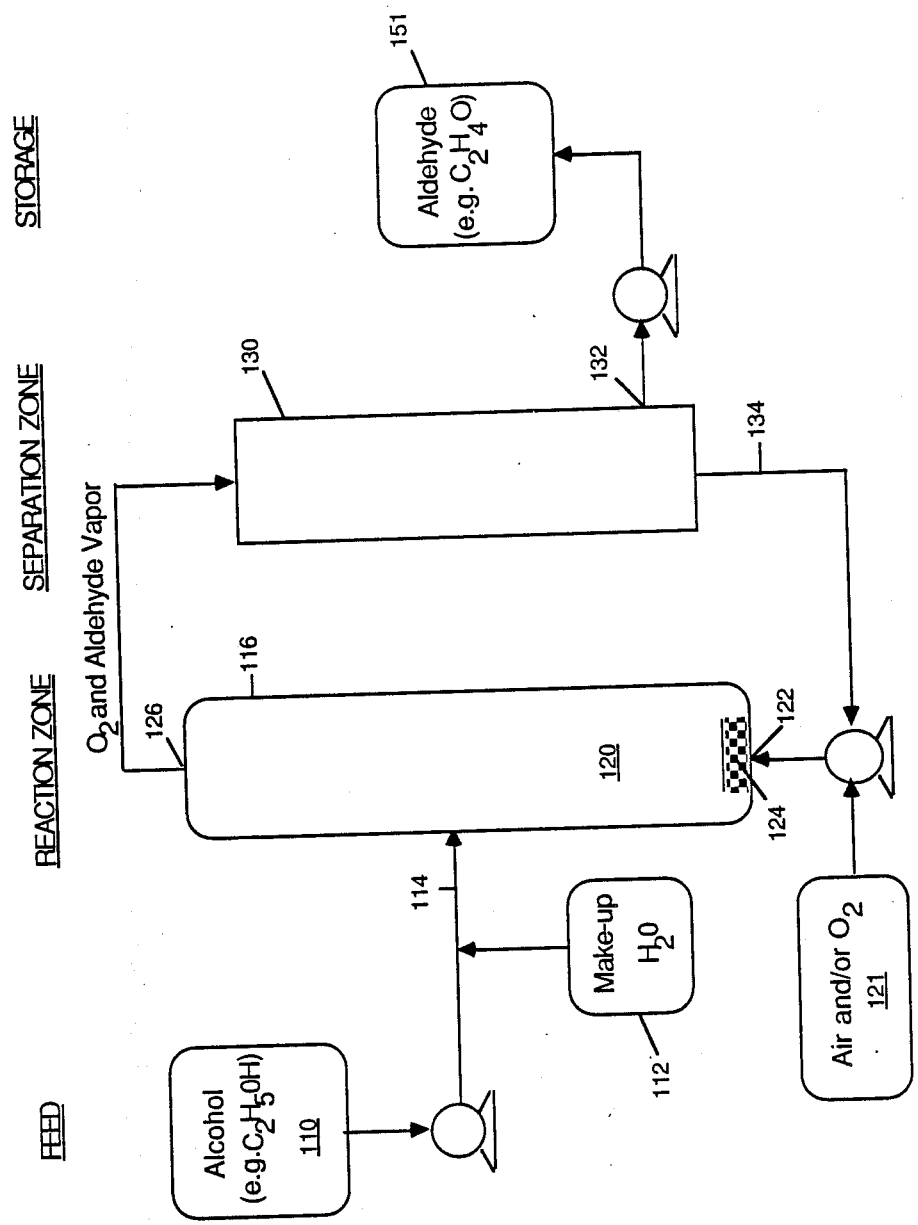
FIG. 2 is a schematic representation of an apparatus for the continuous conversion of alcohol to low boiling point aldehydes.

FIG. 2 illustrates a somewhat different apparatus for production of aldehyde alone. An alcohol source 110 and a water source 112 are fed through an inlet line 114 into a reaction zone 116 which contains a reaction mixture 120. Unlike the apparatus of FIG. 1, the reaction mixture 120 in this case includes catalase, in addition to the water, alcohol, and methanol oxidase enzyme. Oxygen is fed into the reaction zone 116 from an oxygen source 121 through gas inlet 122 through porous material 124 and is removed from the reaction zone 116 through gas outlet 126.

The catalase in the reaction mixture 120 catalyzes the decomposition of hydrogen peroxide to water and oxygen. Thus, the net reaction in this process is the conversion of alcohol to aldehyde with the consumption of oxygen.

Certain aldehydes which can be produced, such as acetaldehyde, have vapor pressures higher than that of water at a temperature at which the methanol oxidase is stable. Thus, significant quantities of aldehyde are removed through the gas outlet 126 with the oxygen leaving the reaction zone 116. In this embodiment of the invention, the gas leaving the reaction zone 116 is directed through the gas outlet 126 into a condenser 130. The condenser 130 condenses the aldehyde and water entrained in the gas leaving the reaction zone into an aqueous aldehyde product which is removed through condenser outlet line 132 to storage vessel 151. Oxygen leaves the condenser 130 through recirculation line 134 and is reintroduced into the reaction zone 116 through gas inlet 122.

The system of FIG. 2 has the advantage of greatly simplifying the separation step of the process because the only product is aldehyde containing some water and minor quantities of alcohol.

Figure 3:
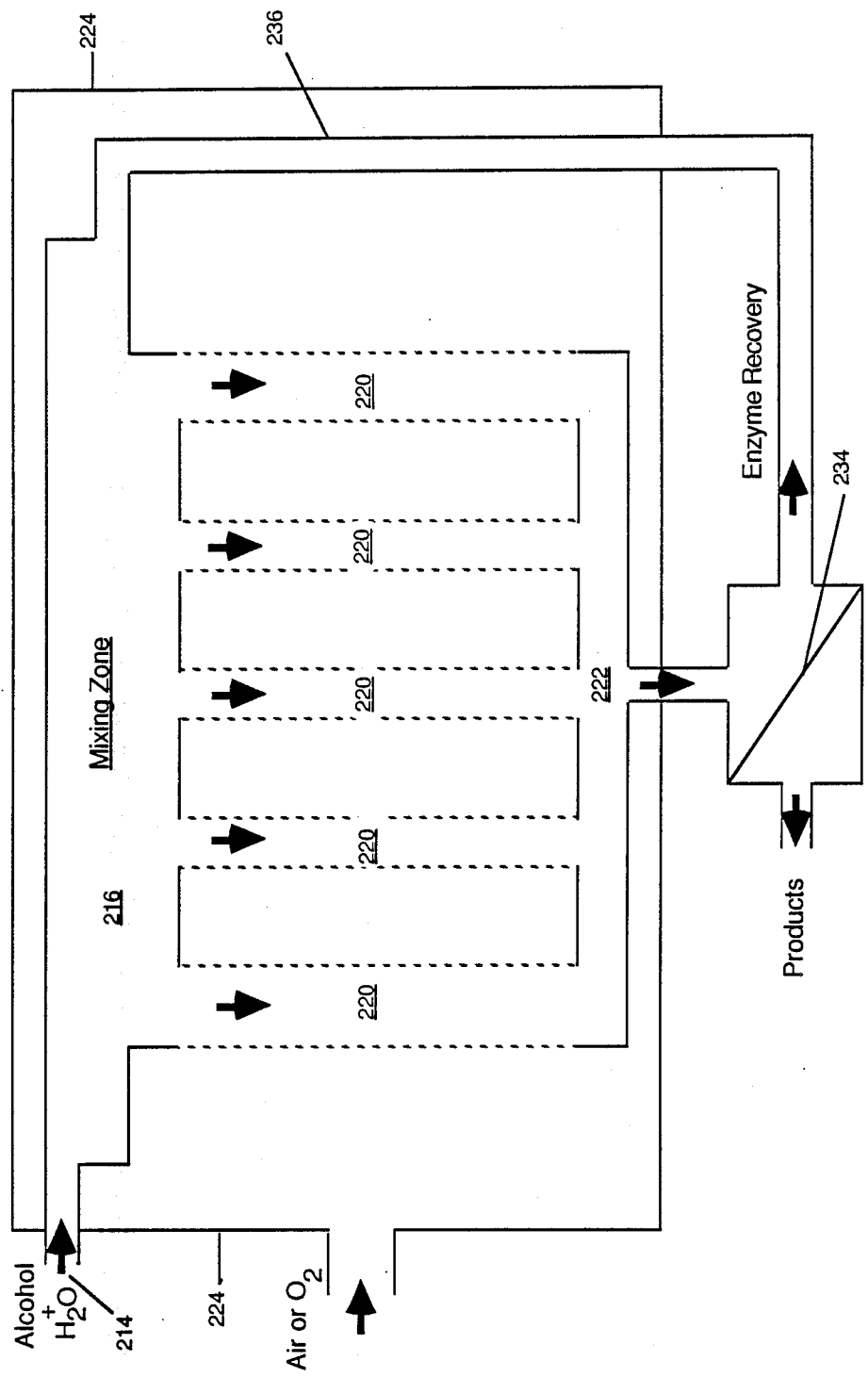
FIG. 3 is a schematic representation of an alternative reaction zone structure wherein alcohol is converted to aldehyde and hydrogen peroxide.

An alternative type of reaction zone structure is shown in FIG. 3. In this embodiment, alcohol and water are introduced through inlet line 214 and are mixed with methanol oxidase enzyme in a mixing zone 216. The alcohol-water-enzyme mixture, comprising a reaction mixture, then flows through one or more tubes 220 (indicated by dashed lines), preferably under generally laminar conditions. The flow rate is controlled so that the conversion of alcohol to aldehyde and hydrogen peroxide is substantially complete by the time the reaction mixture reaches the downstream end 222 of the tubes 220.

Oxygen may be introduced into the mixing zone 216 or into the water and alcohol prior to introducing it into the inlet 214. However, continuous introduction of oxygen into the reaction mixture is preferred. This may be accomplished through the use of gas permeable, water impermeable tubes 220. In this embodiment of the invention, oxygen continuously diffuses through the tube 220 into the reaction mixture, where it is consumed. One suitable gas permeable, water impermeable material is microporous polytetrafluoroethylene of the type marketed by W. L. Gore Company under the trademark GORETEX. The preparation of this material is disclosed in U.S. Pat. Nos. 3,953,566 and 4,187,390. When gas permeable tubes 220 are used, they are preferably enclosed in a pressure vessel 224. Oxygen under pressure is introduced into the pressure vessel 224.

Reaction mixture leaving the downstream end 222 of the tubes 220 passes into an enzyme recovery means 234, which may comprise a dialysis membrane, ultrafiltration material, or other suitable means for separating the enzyme from the remainder of the reaction mixture. Recovered enzyme may be recirculated through line 236 to the mixing zone 216. The entire apparatus from the mixing zone 216 to the enzyme recovery means 234 constitutes the reaction zone in this embodiment of the invention. The reaction mixture becomes depleted in alcohol and the product concentration increases as the reaction mixture moves from one end of the reaction zone to the other. This same result may be achieved by having a reaction zone comprising a plurality of discrete containers, with reaction mixture flowing from container to container, and where the concentration of product increases and the concentration of alcohol decreases as the reaction mixture proceeds through the reaction zone.

We claim:

1. A process for the enzymatic conversion of alcohol to aldehyde and hydrogen peroxide in vitro, comprising the steps of:

introducing water, lower alkyl alcohol or lower alkenyl alcohol, and extracellular methanol oxidase into a reaction zone to form a reaction mixture, wherein said reaction mixture is substantially free from catalase activity;

oxygenating said reaction mixture by contacting at least some of the water in the reaction mixture with an oxygen-containing gas at a pressure greater than atmospheric pressure; and enzymatically converting said alcohol in said reaction mixture into an aldehyde and hydrogen peroxide, wherein the concentration of hydrogen peroxide in said reaction mixture after said enzymatic conversion of said alcohol is greater than about 0.5% weight/volume, wherein said methanol oxidase enzyme has an amino acid sequence that is substantially the same as that of the methanol oxidase produced by *Hansenula polymorpha* ATCC 34438 and having substantially the same product and substrate tolerance properties.

2. The process of claim 1, wherein said reaction zone is pressurized during said oxygenation step.

3. The process of claim 1, wherein said pressure is at least 1.5 atmospheres.

4. The process of claim 1, wherein said pressure is at least 2 atmospheres.

5. The process of claim 1, wherein said reaction mixture is oxygenated by pressurizing said reaction zone and bubbling an oxygen-containing gas through said reaction mixture.

6. The process of claim 1, wherein at least a portion of said reaction zone is a tube and wherein said oxygen-containing gas is introduced into said reaction mixture through the walls of said tube.

7. The process of claim 6, wherein said tube is gas permeable and liquid impermeable.

8. The process of claim 1, wherein said reaction zone comprises a series of discrete containers and said reaction mixture passes sequentially through said containers.

9. The process of claim 1, wherein the maximum alcohol concentration of said reaction mixture during said process is a least 0.5 percent by volume.

10. The process of claim 9, wherein said maximum alcohol concentration is at least 1.0 percent by volume.

11. The process of claim 9, wherein said maximum alcohol concentration is at least 2.0 percent by volume.

12. The process of claim 9, wherein said maximum alcohol concentration is at least 3.0 percent by volume.

13. The process of claim 9, wherein said maximum alcohol concentration is at least 4.0 percent by volume.

14. The process of claim 1, wherein the aldehyde concentration of said reaction mixture leaving said reaction zone is at least 0.5 percent by volume.

15. The process of claim 14, wherein said aldehyde concentration is at least 1.0 percent by volume.

16. The process of claim 14, wherein said aldehyde concentration is at least 2.0 percent by volume.

17. The process of claim 14, wherein said aldehyde concentration is at least 3.0 percent by volume.

18. The process of claim 14, wherein said aldehyde concentration is at least 4.0 percent by volume.

19. The process of claim 1, wherein said hydrogen peroxide concentration is at least 1.0 percent by volume.

20. The process of claim 1, wherein said concentration of hydrogen peroxide is at least 2.0 percent by volume.

21. The process of claim 1, wherein said hydrogen peroxide concentration is at least 3.0 percent by volume.

22. The process of claim 1, wherein said concentration of hydrogen peroxide is at least 4.0 percent by volume.

23. The process of claims 1, 2, 3, 4, 5, 9, or 14, further comprising the step of removing oxygen-containing gas from said reaction zone and recirculating said oxygen-containing gas back into contact with said reaction mixture in said reaction zone.

24. The process of claim 23, further comprising the step of passing said oxygen-containing gas removed from said reaction zone through a condenser to condense liquids out of said oxygen-containing gas before recirculating said oxygen-containing gas back into said reaction zone.

25. The process of claim 23, wherein said oxygen-containing gas is oxygen.

26. The process of claims 1, 9 or 14, wherein said methanol oxidase enzyme is encoded by a methanol oxidase gene having a base sequence differing from that of the gene of *Hansenula polymorpha* ATCC 34438 only by modifications that do not substantially diminish the product and substrate tolerance properties of that enzyme.

27. The process of claims 1, 9, or 14, wherein the methanol oxidase enzyme has an active site identical to that of the methanol oxidase of *Hansenula polymorpha* ATCC 34438.

28. The process of claim 1, 9, or 14, wherein said methanol oxidase enzyme is derived from *Hansenula polymorpha*.

29. The process of claim 28, wherein said methanol oxidase enzyme is derived from *Hansenula polymorpha* ATCC 34438.

30. The process of claim 28, wherein said methanol oxidase enzyme is active in concentrations of 0.5 percent methanol by volume, and 1.0 percent formaldehyde by volume.

31. The process of claim 1, 9, or 14, wherein said alcohol is methanol.

32. The process of claim 1, 9, or 14, wherein said alcohol is ethanol.

33. The process of claim 1, 9, or 14, wherein said alcohol is allyl alcohol.

34. The process of claim 1, 9, or 14, wherein said aldehyde is continuously removed from said reaction zone as a gas.

35. The process of claim 1, 9, or 14, further comprising the step of introducing a catalase into said reaction mixture to catalyze the decomposition of hydrogen peroxide to water and oxygen, so that the net product of the process is aldehyde.

36. The process of claim 35, wherein the aldehyde is formaldehyde.

37. The process of claim 35, wherein the aldehyde is acrolein.

38. The process of claim 35, wherein the aldehyde is acetaldehyde.

39. The process of claim 35, wherein said aldehyde is continuously removed from said reaction zone as a gas entrained in said oxygen-containing gas.

40. The process of claim 39, further comprising the step of condensing said aldehyde out of said oxygen-containing gas and then recirculating said oxygen-containing gas into said reaction zone.

41. The process of claim 39, wherein said aldehyde is acetaldehyde.

42. The process of claim 39, wherein said aldehyde is formaldehyde.

43. The process of claims 1, 2, 3, 4, 5, 6, 9, or 14, wherein said oxygen-containing gas is oxygen.

44. The process of claims 1, 9, or 14, further comprising the step of adjusting the pH of said reaction mixture with a buffer to a pH of from about 7.0 to about 8.0.

45. The process of claim 44, wherein said buffer is a volatile buffer.

46. The process of claim 45, wherein said buffer is a carbonate or bicarbonate buffer.

47. The process of claim 46, wherein said buffer is an ammonium bicarbonate buffer.

* * * * *